US008986608B2

(12) United States Patent
Lam et al.

(10) Patent No.: US 8,986,608 B2
(45) Date of Patent: Mar. 24, 2015

(54) METHOD FOR RADIATION STERILIZATION OF MEDICAL DEVICES

(75) Inventors: Stan Lam, Pleasanton, CA (US); James Wise, San Bruno, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 964 days.

(21) Appl. No.: 13/109,749

(22) Filed: May 17, 2011

(65) Prior Publication Data

US 2012/0294759 A1 Nov. 22, 2012

(51) Int. Cl.
*G01N 23/00* (2006.01)
*A61N 5/00* (2006.01)
*A61L 2/00* (2006.01)
*A61L 2/08* (2006.01)

(52) U.S. Cl.
CPC .............. *A61L 2/087* (2013.01); *A61L 2/081* (2013.01); *A61L 2/082* (2013.01); *A61L 2202/21* (2013.01)
USPC ................. 422/22; 250/453.11; 250/492.1

(58) Field of Classification Search
CPC .............. A61L 2/00; A61L 9/18; A61L 9/20
USPC ............................ 422/22; 250/453.11, 492.1
See application file for complete search history.

(56) References Cited

U.S. PATENT DOCUMENTS

| RE23,195 E | 2/1950 | Brasch |
| 6,806,476 B2 | 10/2004 | Rose et al. |
| 7,776,926 B1 | 8/2010 | Hossainy et al. |
| 7,959,857 B2 | 6/2011 | Freeman et al. |
| 2003/0190272 A1* | 10/2003 | Raine et al. ................... 422/300 |
| 2003/0215354 A1 | 11/2003 | Clark et al. |
| 2005/0013729 A1 | 1/2005 | Brown-Skrobot et al. |
| 2005/0233062 A1 | 10/2005 | Hossainy et al. |
| 2006/0067974 A1 | 3/2006 | Labrecque et al. |
| 2007/0065334 A1 | 3/2007 | Shalaby |
| 2007/0280851 A1 | 12/2007 | Freeman et al. |

(Continued)

FOREIGN PATENT DOCUMENTS

| EP | 0 218 003 | 4/1987 |
| JP | 11 133196 | 5/1999 |
| JP | 2000 334028 | 12/2000 |

(Continued)

OTHER PUBLICATIONS

International Search Report for PCT/US2007/0129930 filed Jun. 1, 2007, mailed Dec. 18, 2007, 5 pgs.

*Primary Examiner* — Monzer R Chorbaji
(74) *Attorney, Agent, or Firm* — Squire Patton Boggs (US) LLP

(57) ABSTRACT

Sterilization of medical devices can be performed by stacking packages containing the medical devices. The packages are arranged in a partially-overlapping orientation which is at an oblique angle to the direction of irradiation. The partially-overlapping orientation and oblique angle are predetermined for high sterilization throughput and tight control of irradiation. Instead arranging the packages directly on a sterilization platform at a sterilization facility, the packages can be stacked in the partially-overlapping orientation into a transport box at a location remote from the sterilization facility. The transport box maintains the orientation of the packages. Thereafter, the transport container is placed on the sterilization platform, which results in greater uniformity in radiation exposure while maintaining a high level of sterilization throughput.

24 Claims, 8 Drawing Sheets

(56) References Cited

U.S. PATENT DOCUMENTS

2008/0299002 A1* 12/2008 Freeman et al. ............... 422/22
2011/0066222 A1   3/2011 Wang et al.

FOREIGN PATENT DOCUMENTS

| WO | WO 03/037390 | 5/2003 |
| WO | WO 2006/034157 | 3/2006 |

* cited by examiner

METHOD FOR RADIATION STERILIZATION OF MEDICAL DEVICES

FIELD OF THE INVENTION

Disclosed herein are methods and apparatuses for sterilization of medical devices using radiation.

BACKGROUND OF THE INVENTION

Medical devices can be sterilized in various ways, such as by gas and radiation. Gas sterilization may not be suitable for various reasons. For example, there may be a need to sterilize tight or closed confines of the medical device which cannot be reached by the sterilizing gas with sufficient reliability. Also, the use of gas may result in undesirable chemical reactions with drugs or materials of the medical device. Packaging required for some medical devices may also limit the effectiveness of gas sterilization. Accordingly, it may be more desirable or necessary to sterilize some medical devices using radiation, such as electron beam (E-beam), gamma radiation, ion beam, and x-ray.

Some forms of radiation have been used to sterilize conventional metal stents. A stents is a type of endoprosthesis that is implanted in an anatomical lumen. An endoprosthesis is an artificial device that is placed inside a human or animal body. An anatomical lumen is a cavity of a tubular organ such as a blood vessel. Stents are generally cylindrically shaped devices, which function to hold open and sometimes expand a segment of a blood vessel or other anatomical lumen such as urinary tracts and bile ducts. Stents are often used in the treatment of atherosclerotic stenosis in blood vessels. In such treatments, stents reinforce body vessels and prevent restenosis following angioplasty in the vascular system.

Radiation used for sterilization can have a negative effect on the chemical, mechanical and other properties on the item being sterilized if radiation exposure is not controlled. There is often a greater need to minimize such negative effects for stents as compared to other types of medical devices. This is because of the unique structural and functional requirements imposed on stents.

Stents are relatively small, as they are often required to be passed through tight confines of anatomical lumens. A stent must often have great longitudinal flexibility to allow it to pass through tortuous curves of anatomical lumens. Stents typically comprise a fine network of struts which form a tubular scaffold. The tubular scaffold must often be capable of being crimped onto a delivery device, such as a balloon, to reduce its size to allow passage through anatomical lumens, and then forcibly expanded by the balloon to an enlarged, deployed state at the desired location within the body. For some stents, the tubular scaffold must be capable of self-expanding from its crimped state at the desired location within the body. After implantation and deployment, the tubular scaffold must have sufficient strength to support surrounding anatomical structures upon implantation. Thus it will be appreciated that stents present unique challenges in controlling radiation exposure to minimize negative effects on the stent while at the same time reducing the bioburden of the stent to an acceptable sterility assurance level (SAL).

Also, polymers are often more susceptible to negative effects of radiation sterilization than metals. Some polymer stents are designed to biodegrade after implantation and it may be desirable that the stent degrade or dissolve at a particular rate. Thus, the advent of polymer stent can present even greater challenges. An example of a polymer stent and method of manufacture is provided in U.S. application Ser. No. 12/558,105, filed Sep. 11, 2009 (Publication No. 2011/0066222), the entirety of which is incorporated herein by reference.

Additionally, an active or bioactive drug may be contained in a coating on a stent or within polymer struts of a stent. The drug may be required to elute at a particular rate upon implantation. Certain drugs may be sensitive to radiation or heat induced by radiation exposure. Thus, the need to prevent degradation of the drug can present further challenges.

Furthermore, the cost of sterilization is lowered when the number of stents sterilized over a period of time (i.e., sterilization capacity or throughput) is increased. Thus, a further challenge is to develop ways to increase efficiency of radiation sterilization procedures while at the same time maintaining acceptable sterility assurance levels and reducing negative effects of radiation sterilization on stents.

Accordingly, there is a continuing need for methods and apparatuses for radiation sterilization of medical devices which allow for greater control of radiation exposure in order maintain acceptable sterility assurance levels, minimize negative effects on the medical device, and increase sterilization throughput.

SUMMARY OF THE INVENTION

Briefly and in general terms, the present invention is directed to a method of sterilizing medical devices.

In an aspect of the present invention, the method comprises placing packages into a transport container, each package containing at least one medical device, the packages partially shielding each other, each package having a corner portion with two exposed corner surfaces that are not shielded by an adjacent package and are out of contact with the transport container, the transport container having an interior space occupied by the packages, the interior space sized to keep the packages from shifting in position within the transport container when the transport container is in a closed state. Next, the method further comprises sending the transport container, with the packages therein, to a sterilization facility.

In an aspect of the present invention, the method comprises stacking packages side-by-side in a transport container such that a first side of each package includes a contact surface portion, in contact with an adjacent package or a dummy load, and an exposed surface portion, not in contact with the adjacent package nor the dummy load, the transport container having an interior space occupied by the packages, the interior space sized to keep the packages from shifting in position within the transport container when the transport container is in a closed state.

The features and advantages of the invention will be more readily understood from the following detailed description which should be read in conjunction with the accompanying drawings.

DETAILED DESCRIPTION OF THE INVENTION

As used herein, any term of approximation such as, without limitation, near, about, approximately, substantially, essentially and the like mean that the word or phrase modified by the term of approximation need not be exactly that which is written but may vary from that written description to some extent. The extent to which the description may vary will depend on how great a change can be instituted and have one of ordinary skill in the art recognize the modified version as still having the properties, characteristics and capabilities of the modified word or phrase. For example without limitation, a surface that is described as "substantially flat" refers to a surface that is perfectly flat and a surface that one skilled in the art would readily recognize as being flat even though points on the surface are at different elevations. As another non-limiting example, a feature described as "about the same" as another feature encompasses the condition wherein the two features are exactly the same and a condition that one skilled in the art would readily recognize as being the same even though the features are not exactly the same. In general, but with the preceding discussion in mind, a numerical value herein that is modified by a word of approximation may vary from the stated value by ±15%, unless expressly stated otherwise.

It is generally desired to irradiate each medical device with a level of radiation that falls within a specified range of radiation exposure. This is of particular importance for polymeric stents, since exposure to radiation above a specified range can cause undesirable degradation of chemical and mechanical properties of a polymer. The methods discussed herein reduce the likelihood of irradiation outside a specified range.

Radiation sterilization processes may have inherent variability in the amount of radiation that is applied from medical device to medical device being sterilized. The variability can arise from changes in orientation of the product relative to the radiation source, slight differences in the position of the medical device relative to the radiation source, the amount of material shielding the medical device from the radiation source, and the amount of backscatter radiation due to the surrounding environment. The methods described herein minimize these and other variables to effect tighter control of radiation exposure and increase uniformity of exposure.

Figure 1:
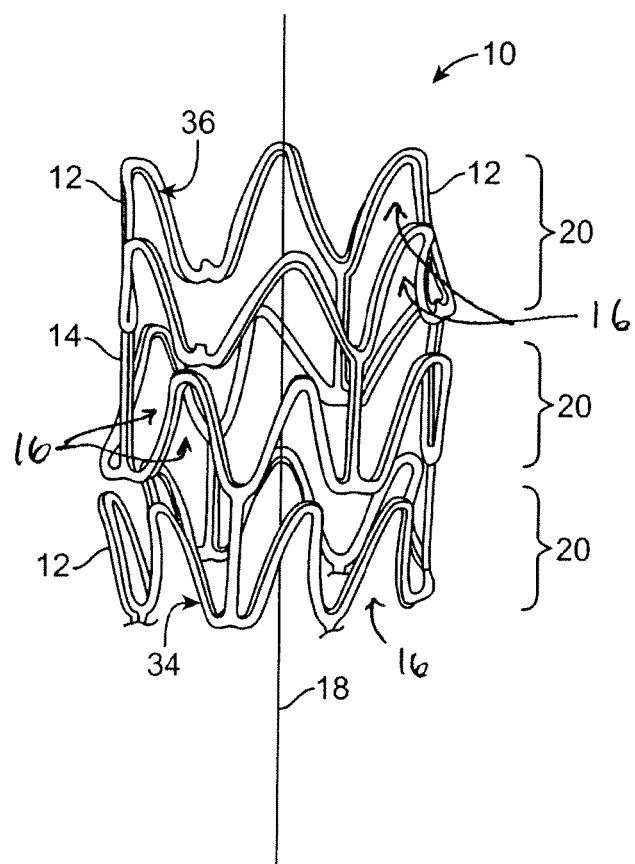
FIG. 1 is a partial perspective view of a stent.

Referring now in more detail to the exemplary drawings for purposes of illustrating embodiments of the invention, wherein like reference numerals designate corresponding or like elements among the several views, there is shown in FIG. 1 an upper portion of stent 10 having an overall body shape that is hollow and tubular. The stent can be balloon expandable or self-expandable. The present invention encompasses stents having any particular geometrical configuration, such as a zig-zag, sinusoidal or serpentine strut configuration, and should not be limited to the patterns illustrated herein. The variation in stent patterns is virtually unlimited.

Figure 2:
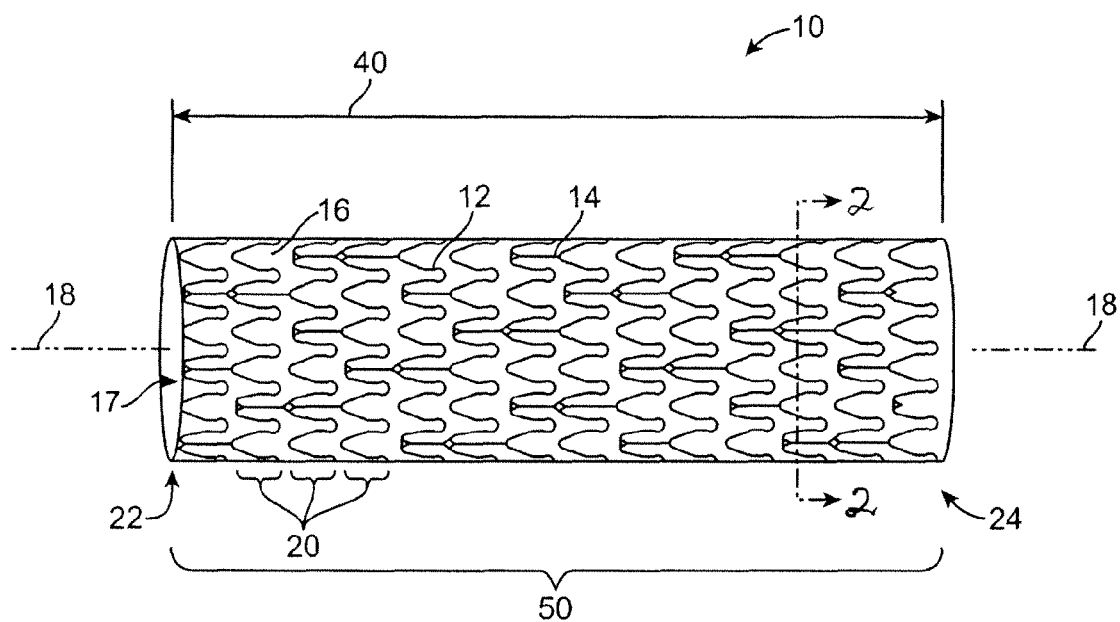
FIG. 2 is a perspective view of another stent.

FIGS. 1 and 2 show stents with two different stent patterns. The stents are illustrated in a state before crimping (non-crimped state) or after expansion (expanded state). In both FIGS. 1 and 2, stent 10 includes many interconnecting struts 12, 14 separated from each other by gaps 16. Struts 12, 14 form a tubular frame and can be made of any suitable material, such as a biocompatible metal or polymer.

Stent 10 has an overall longitudinal length 40 measured from opposite ends, referred to as proximal and distal ends 22, 24. Stent 10 has overall body 50 having a tube shape with central passageway 17 passing through the entire longitudinal length of stent 10. Central passageway 17 has two circular openings, there being one circular opening at proximal end 22 and distal end 24. Central axis 18 runs through central passageway 17 in the center of tubular frame body 50. At least some struts 12 are arranged in series to form sinusoidal or serpentine ring structures 20 that encircle central axis 18. Ring structures 20 are connected to each other by other struts 14, referred to as links, that are substantially straight and are oriented longitudinally in a direction parallel to central axis 18. Ring structures 20 are configured to be crimped and subsequently radially expanded.

Figure 3:
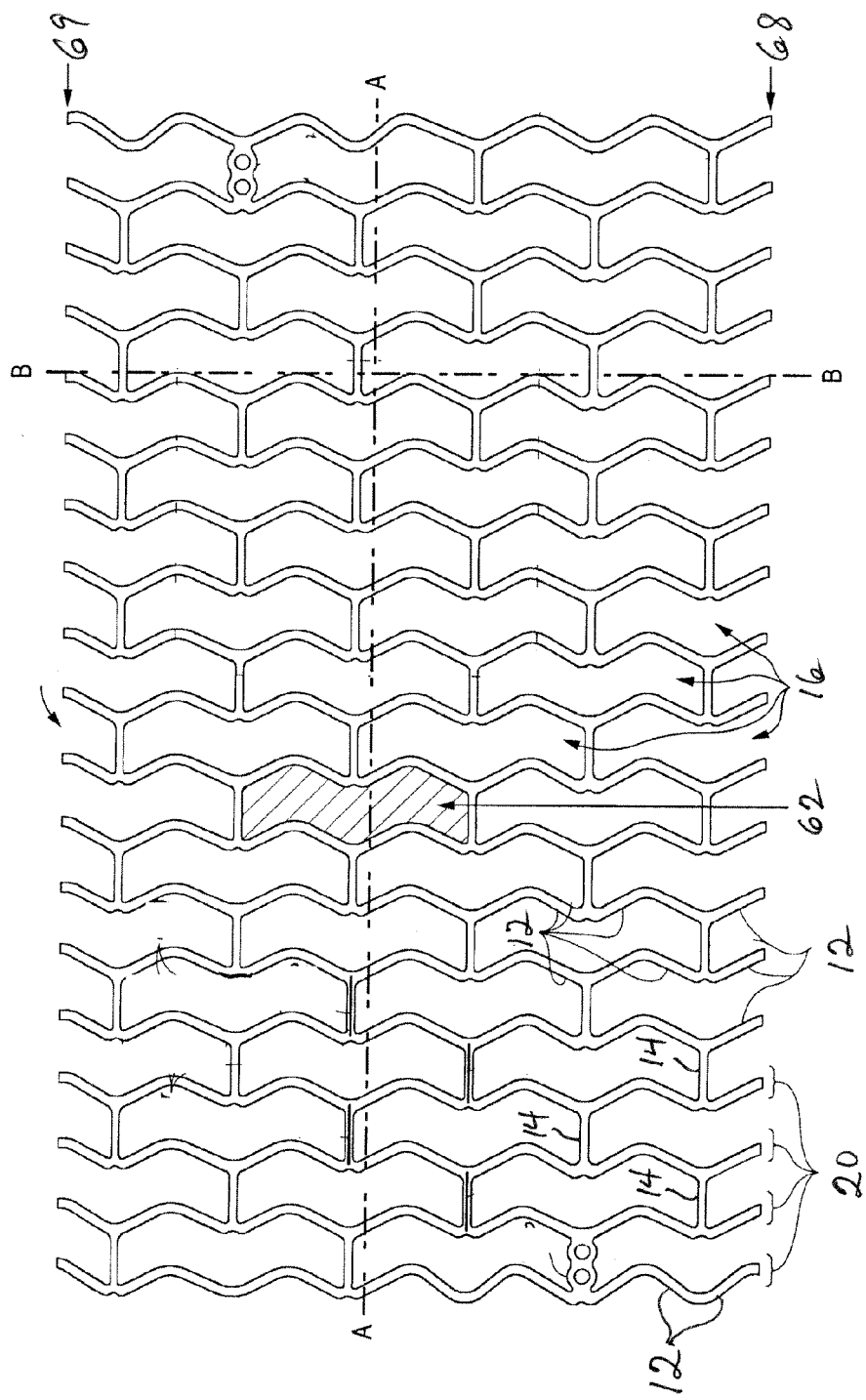
FIG. 3 is an artificially flattened view of a pattern of struts for another stent.

FIG. 3 shows another stent pattern 60 illustrated in a planar or flattened view for ease of illustration and clarity. The stent pattern 60 was cut from a tubular precursor construct. Thus, stent pattern 60 actually forms a tubular stent structure so that line A-A is parallel to the central axis of the stent. Stent pattern 60 includes various struts 12, 14 oriented in different directions, there being gaps 16 between the struts. Gaps 16 and struts 12, 14 define W-shaped closed cells 62. One such closed cell 62 is shown with cross-hatch lines to illustrate the shape and size of the cells. All the cells 62 have the same size and shape.

Pattern 60 is illustrated with bottom edge 68 and top edge 69. On the actual stent, bottom edge 68 meets top edge 69 so that line B-B forms a circle around the stent central axis. In this way, stent pattern 60 actually forms sinusoidal hoops or rings 20, each of which include a series of struts 12 arranged circumferentially. Rings 20 are connected to each other by another group of struts 14 that are substantially parallel to line A-A and the central axis of the stent. Rings 20 are capable of being collapsed to a smaller diameter during crimping and then expanded to their original diameter or to a larger diameter during deployment in an anatomical blood vessel or other anatomical lumen. Further details of stent pattern 60 can be as described in U.S. patent application Ser. No. 12/114,608, filed May 2, 2008 (Publication No. 2008/0275537), the entirety of which is incorporated herein by reference.

The material used to make the structural substrate of the above described stents and strut patterns can be non-bioabsorbable or bioabsorbable. As used herein, the terms "bioabsorbable" and "biodegradable" are used interchangeably and refer to materials that are capable of being absorbed or degraded when exposed to bodily fluids such as blood, and components thereof such as enzymes, and that can be gradually resorbed, absorbed, and/or eliminated by the body. Suitable examples of bioabsorbable polymer include without limitation poly(L-lactide) ("PLLA") and poly(L-lactide-co-glycolide) ("PLGA"). Other suitable materials include those described in U.S. application Ser. No. 12/558,105.

Additionally, a polymer-based coating can be applied on the stent substrate. The coating can be a biodegradable polymer or combination of biodegradable polymers, a biostable polymer or combination of biostable polymers, or a combination of biodegradable and biostable polymers. The coating and/or the stent substrate material may also include a drug or active agent. Drugs and active agents can include any substance capable of exerting a therapeutic, prophylactic, or diagnostic effect.

Figure 4:
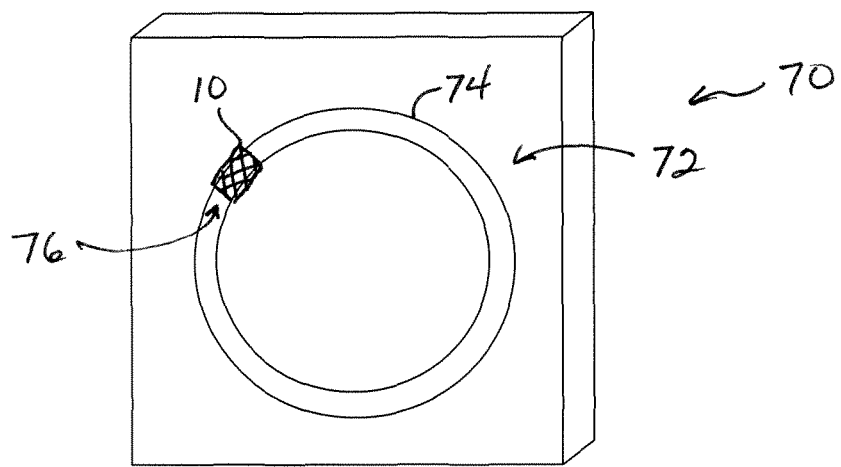
FIG. 4 is a perspective view of a package, showing the orientation and location of a stent-catheter assembly contained within the package.

FIG. 4 shows a diagram of a sealed package 70 ready for sterilization. Package 70 is a rectangular box. Inside package 70 there is an assembly 71 which comprises catheter 72 and stent 10 mounted on catheter 72. The catheter 72 includes tube 74 and inflatable balloon 76 on which stent 10 is crimped. Tube 74 is coiled in a circular fashion within package 70. Stent 10 can be any type of stent, including those describe in connection with FIGS. 1-3. Package 70 can include a conventional sealable, flexible metallic or plastic pouch, used for storage and shipping stent-catheter assembly 71, and a relatively rigid chipboard box which carries the pouch. Package 70 protects the assembly from exposure to air, moisture, and light.

Figure 5:
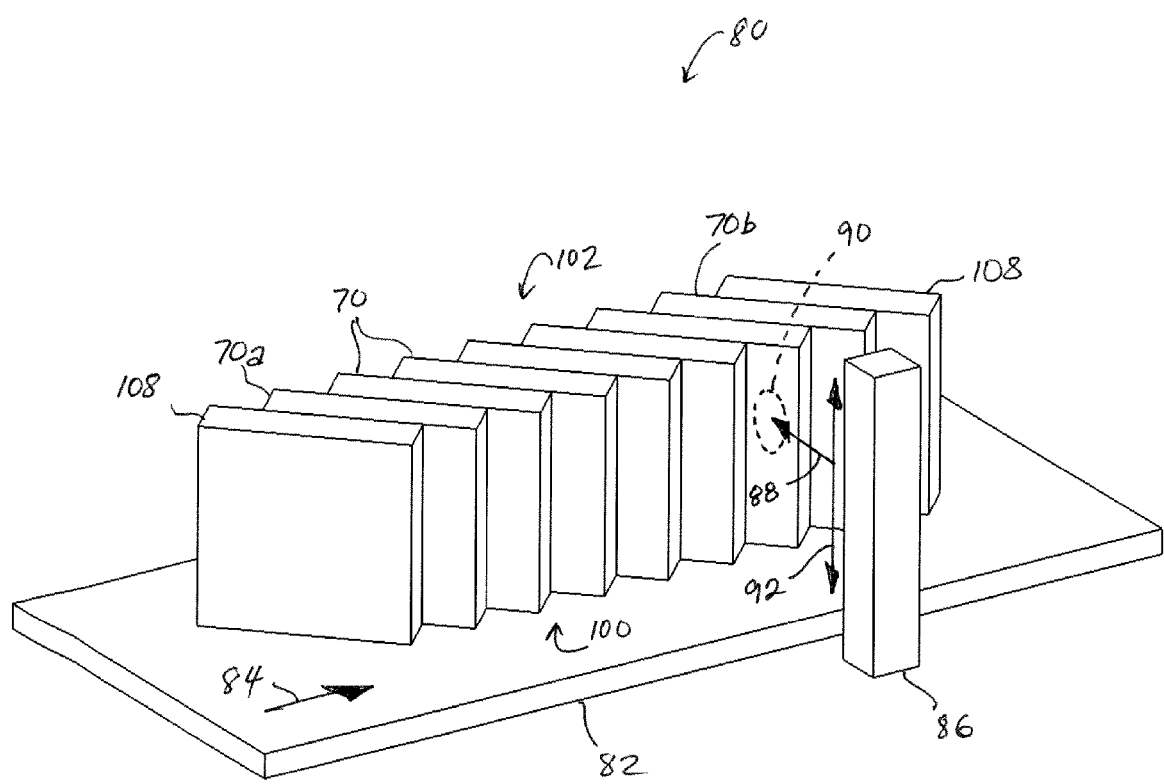
FIG. 5 is a perspective view of an E-beam sterilization apparatus, showing a stack of packages in a partially-overlapping and tilted arrangement on the sterilization apparatus.

FIG. 5 shows a diagram of an E-beam sterilization apparatus 80. Multiple packages 70 are placed on a horizontal sterilization platform 82 that moves linearly at a controlled velocity in the direction of arrow 84. Sterilization platform 82 moves sealed packages 70 toward radiation source 86. The radiation source emits an E-beam in the direction of arrow 88, which is perpendicular to the direction of arrow 84. Arrow 88 passes through the center of the E-beam and represents the central axis of the E-beam. As packages 70 move across and in front of radiation source 86, the E-beam radiation intersects packages 70. The E-beam radiation has a circular cross-sectional shape so that only limited region 90 of sealed packages 70 is exposed to radiation at a particular instant of time. Radiation source 86 is configured in such a way that causes the E-beam to move continuously, back and forth, in vertical directions along arrow 92. The continuous up and down movement of the E-beam results in all surfaces of each package 70 to be exposed to radiation as sterilization platform 82 passes completely across radiation source 86.

In other embodiments, sterilization platform 82 is stationary and radiation source 86 moves in the direction of arrow 84 in front of sterilization platform 82 in order to expose all surfaces of each package 70 to radiation.

Figure 6:
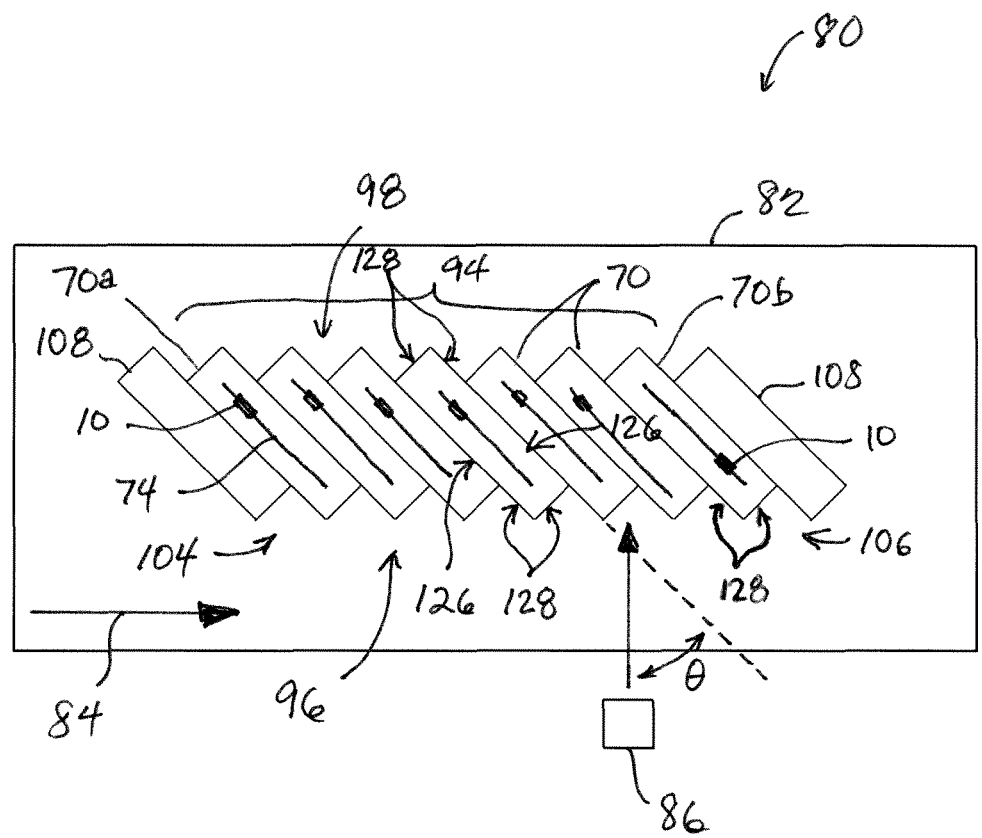
FIG. 6 is a top view of the E-beam sterilization apparatus of FIG. 5, showing the orientation of stent-catheter assemblies relative to the sterilization apparatus.

FIG. 6 shows a top view of the sterilization setup of FIG. 5. Packages 70 are arranged in an overlapping fashion so as to increase sterilization throughput. Packages 70 only partially overlap each other, so that two surfaces of a corner portion of each package 70 are unshielded from and directly exposed to radiation source 86. Packages 70 form stack 94 in which they are in face-to-face contact with each other. Each package 70 is tilted at angle θ. The tilt angle θ is an oblique angle, defined herein as not zero degrees and not ninety degrees. Packages 70 are tilted so that they do not completely overlap each other with respect to the direction of radiation exposure of arrow 88.

In one embodiment, tilt angle θ is about 45 degrees in order to provide a balance between the need for uniformity in radiation exposure and high sterilization throughput. In other embodiments, tilt angle θ can be more acute (reduced to less than 45 degrees), which results in a tighter packing arrangement and, thus, increased sterilization throughput. Applicants have found, however, that a more acute tilt angle θ can also result in a greater amount of radiation backscatter and, thus, less uniformity in radiation exposure from stent to stent.

In the illustrated embodiment, the tilt angle θ is the angle between a primary side of package 70 and the direction of radiation exposure of arrow 88. The primary side is defined as the side or exterior face of package 70 which has the largest surface area. In other embodiments, where the primary side of packages 70 is irregular in shape, the tilt angle θ can be the angle between a reference plane, which approximates the direction of the primary side, and the direction of radiation exposure of arrow 88.

Stack 94 has front 96 which faces the radiation source, rear 98 which faces away from the radiation source, bottom 100 (FIG. 5) which rests on sterilization platform 82, top 102 (FIG. 5) which faces upward, and ends 104, 106 which face to the left and right of radiation source 86. Dummy loads 108 are placed at ends 104, 108 of stack 94 so that the packages 70a, 70b at ends 104, 108 are exposed to the same or about the same level of radiation as packages 70 in the middle of stack 94, thereby increasing uniformity in the amount of radiation that is applied from package to package. Dummy loads 108 match, simulate or approximate radiation absorbance and/or radiation reflectivity of one or more packages 70 and medical devices contained therein.

In the illustrated embodiments, dummy loads 108 are about the same size and shape as packages 70. In other embodiments, dummy loads 108 are larger or smaller than packages 70. The size of dummy loads 108 can depend upon the shielding characteristics of the material from which dummy loads 108 are made. Also, the size of dummy loads 108 relative to packages 70 can depend on the density of package 70 and its contents in relation to the density of the material from which dummy loads 108 are made. Dummy loads 108 can be hollow or be a solid, unitary piece of material. Dummy loads 108 can be made from a variety of materials, suitable examples of which include without limitation polyethylene foam, polyurethane foam, and other solid foam of synthetic polymer material. In presently preferred embodiment, dummy loads made entirely of foam (such as polyethylene foam) having a density of about 96 kg/m$^3$ are used when each package 70 has an average density of about 0.1 g/cm$^3$.

Referring to FIGS. 5 and 6, each package 70 has contact surfaces 126 that touch and are shielded by an adjacent package 70 or dummy load 108, and exposed surfaces 128 which do not touch any adjacent package 70 or dummy load 108. The contact surfaces 126 and exposed surfaces 128 are the same, in terms of area size and location, from one package 70 to the next.

Packages 70 within stack 94 are arranged in such a way that stents 10 within the packages are located closer to rear 98 of the stack than front 96 of the stack. Applicants have found that stents located in this manner allow for sterilization of the entire stent-catheter assembly 71 (combination of stent 10 and catheter 72) to a desired sterility assurance level while minimizing degradation to the stent. For example, catheter 72 may be able to sustain radiation exposure up to 50 kGy without significant degradation of performance, but stent 10 can be more sensitive than catheter 72, so package 70 can be oriented such that stent 10 receives a level of radiation less than 50 kGy but is nonetheless sterilized to the needed sterility assurance level.

It will be appreciated that some parts of stent-catheter assembly 71, such as portions of catheter 72 close to front 96 of stack 94, can become exposed to more radiation than stent 10 located close to rear 98 of stack 94. This is because parts near front 96 have less material shielding them from radiation source 86. Therefore, parts of a medical device that are less sensitive to degradation from radiation can be placed closer to front 96 of stack 94 and parts that are more sensitive to degradation from radiation can be placed closer to rear 98 of stack 94.

In other embodiments of the present invention, stent 10 of stent-catheter assembly 71 is oriented such that it is close to the front 96 of stack 94 and thus closer to radiation source 86. See for example stent 10 in package 70b in FIG. 6. With this orientation, the radiation which reaches stent 10 in package 70b is subjected to less interaction with packaging materials, which allows for tighter distribution of the radiation dose to the stent. Less interaction, such as less shielding and/or less scattering of radiation, results in greater uniformity in radiation dose from stent to stent. Thus, tight control of radiation exposure of stent 10 can be achieved by orienting package 70 within stack 94 in a manner which minimizes shielding and scattering of radiation directed toward stent 10. It will be appreciated that all stents 10 in stack 96 can be oriented in the manner shown for package 70b.

The partially-overlapping arrangement of packages 70, tilt angle θ, location of stents 10 within packages 70, construction of dummy loads 108, radiation dosages (measured, for example, in terms of kGy), number of passes across radiation source 86, and other process variables can be as described U.S. patent application Ser. No. 11/809,511, filed Jun. 1, 2007 (Publication No. 2008/0299002), the entirety of which is incorporated herein by reference.

In one embodiment of the invention, stent 10 is manufactured, crimped onto catheter 72, and sealed within package 70 at a facility (such as a manufacturing facility) that is separate and remote from the sterilization facility. Packages 70 containing stent-catheter assemblies 71 are transported from the manufacturing facility to the sterilization facility. Thereafter, personnel at the sterilization facility perform the steps of:

(a) forming stack 94 of packages 70 which have not yet been sterilized;

(b) placing dummy loads 108 at ends 104, 106 of stack 94;

(c) orienting packages 70 such that stents 10 are at the desired location; and (d) ensuring that packages 70 are at the desired tilt angle.

An advantage of performing the above steps at the sterilization facility is that it allows shipping containers and trucks to be filled with packages 70 at any orientation which will maximize the number of packages 70 in the containers and trucks, and without any requirement to have packages 70 tilted or packed with dummy loads 108. Without the tilting angle θ, unused space within the shipping containers and trucks is minimized, which increases transportation efficiency. A potential drawback to the above procedure is that it relies on personnel at the sterilization facility to perform steps which are important to achieving tight control of radiation exposure. An error in performing any one or more of steps (a) through (d) above may result in too little or too much radiation exposure.

Some sterilization facilities are more familiar with sterilizing items which are not sensitive to effects of radiation as compared to medical devices, especially polymer stents. For items having less radiation-sensitivity, the radiation dose can be set at a high level to ensure that the desired sterility assurance level is achieved for each item, even with high variability in radiation exposure from item to item. Thus, at some sterilization facilities, personnel can be unaccustomed to loading items on sterilization platform 82 with the accuracy and uniformity necessary for items which are more radiation-sensitive. With sterilization facilities such as these, the procedure below can be used.

To improve control of radiation exposure, steps (a) through (d) above can be initiated remotely from the sterilization facility. For example, steps (a) through (d) can be initiated at a point in time prior to arrival at the sterilization facility. That is, steps (a) through (d) are not entirely performed at the sterilization facility and are not performed on or near sterilization platform 82. Steps (a) through (d) can be performed, at least in part, at the facility which manufactures stents 10. As described below, steps (a) through (d) can be performed with the aid of a transport container of a predetermined size and shape.

Figure 7:
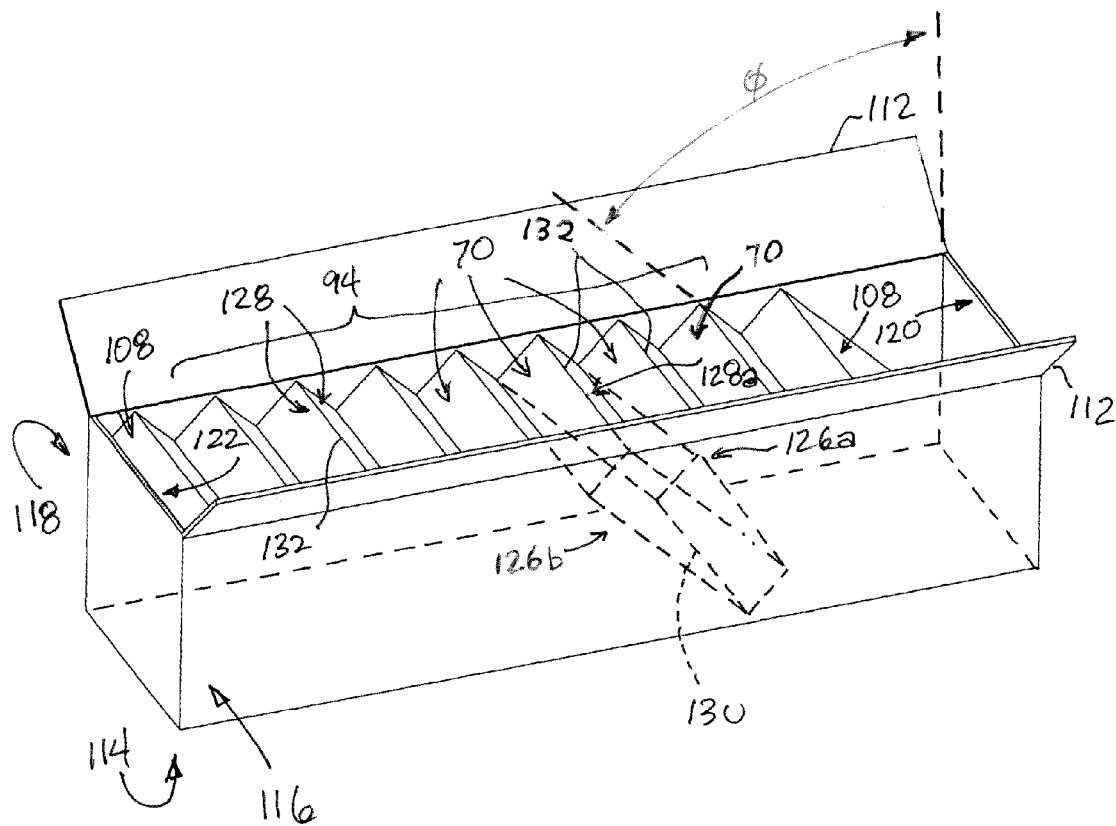
FIG. 7 is a perspective view of a transport container, showing a stack of packages in a partially-overlapping and tilted configuration contained within the transport container.

As shown in FIG. 7, in one embodiment of the invention, a particular number of packages 70 are arranged in stack 94 in transport container 110. Packages 70 have not been sterilized at this point. Transport container 110 is a rectangular box having a movable lid 112, rear face 114, top face 116, bottom face 118, first end face 120, and second end face 122. Rear face 114 is located opposite lid 112. Top face 116 is located opposite bottom face 118. First end face 120 is located opposite second end face 122. Lid 112 and each of the faces comprise substantially flat surfaces. Lid 112 is hinged and is an integral part of transport container 110. In other embodiments, lid 122 is removable from the remainder of transport container 112.

Lid 112 is pivoted opened (as shown in FIG. 7) to allow packages 70 and dummy loads 108 to be placed in transport container 110. Transport container 110 is configured in such a way that when the correct number of packages 70 are stacked together within it and when dummy load 108 is placed at each end of stack 94, the result is that packages 70 and dummy loads 108 are able to slip relative to each other and tilt to angle φ relative to end face 120. Tilt angle φ is an oblique angle, defined herein as not zero degrees and not ninety degrees. When lid 112 is closed, packages 70 and dummy loads 108 are prevented from moving in such a way that allows angle φ to change. For example, when lid 112 is closed, angle φ cannot possibly change more than 5 degrees, and more narrowly 2 degrees. Each package 70 within stack 94 is arranged in such a way that stents within the packages are located closer to rear face 114 than lid 112 of transport container 110.

Referring again to FIG. 7, one of packages 70 is illustrated with broken lines to show an outline of its outer edges. When lid 112 is closed, first edge 130 of each package 70 rests upon rear face 114, and second edge 132 of each package 70 either touches or is close to touching lid 112 when lid 112 is closed. When lid 112 is closed, packages 70 are prevented from shifting in position relative to each other within transport container 110 even with rotation, tipping, tilting, or other movement of transport container 110. The dimensions of the interior space of transport container 110 are carefully selected, based at least on the size and number of packages 70 and size of dummy loads 108, so that the tilt angle φ is maintained during movement and handling of transport container 110 from the manufacturing facility to the sterilization facility.

As shown in FIG. 7, each package 70 has exposed surfaces 128 which do not touch any adjacent package 70 or dummy load 108. Exposed surfaces 128 do not touch any part of transport container 110. Exposed surfaces 128, also referred to as corner surfaces, intersect each other at second edge 132 at an angle of about ninety degrees. When lid 112 is closed, only second edge 132 is capable of touching any part of transport container 110. Each package has contact surfaces 126 that touch and are shielded by an adjacent package 70 or dummy load 108. One of the contact surfaces 126a and one of the exposed surfaces 128a form a primary side of each package 70. That is, the primary side comprises contact surfaces 126a and exposed surfaces 128a. Furthermore, the contact surfaces 126 and exposed surfaces 128 are the same, in terms of area size and location, from one package 70 to the next.

The present invention is not limited to any particular internal dimensions for transport container 110. The internal dimensions can be determined or altered as a function of the size and number of packages 70 and dummy loads 108 and the desired tilt angle φ. In particular, the interior length and interior depth of transport container 110 can depend upon the size and number of packages 70 and dummy loads 108 and the desired tilt angle φ. The interior width of transport container 110 can be the same as the dimension of package 70 along its first edge 130. For example and not limitation, a transport container having interior dimensions of 16 inches (interior width)×59.5 inches (interior length)×14.2 inches (interior depth) can be used to hold seven packages having exterior dimensions of 16 inches×16 inches×4 inches and two dummy loads having exterior dimensions 16 inches×16 inches×4 inches in order to maintain a tilt angle φ of about 45 degrees, as shown in FIG. 7.

Figure 8:
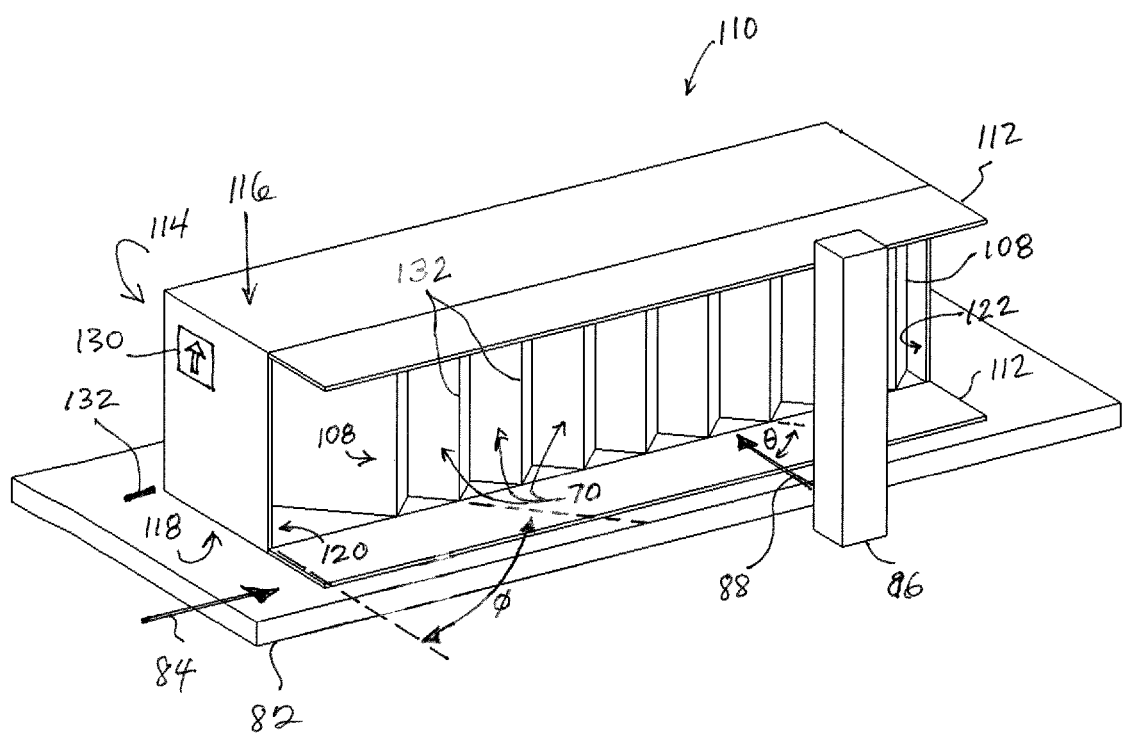
FIG. 8 is a perspective view of the E-beam sterilization apparatus of FIG. 5, showing the transport container of FIG. 7 oriented on the sterilization apparatus in a way that simulates process conditions of FIGS. 5 and 6.

Referring now to FIG. 8, at the sterilization facility transport container 110 is placed on sterilization platform 82. Bottom face 118 of transport container 110 faces down and rests on sterilization platform 82. Top face 116 of transport container 110 faces up. Rear face 114 faces away from radiation source 86, so that stents 10 within the packages are oriented in the same manner described in connection with FIG. 6—that is, stents 10 are located closer to the rear of the stack (away from the radiation source) than the front the stack. Lid 112 or the container opening faces radiation source 86 and is kept open so that lid 112 does not block radiation directed at packages 70. Also, transport container 110 is oriented on sterilization platform 82 so that tilt angle φ within transport container 110 is the same as the desired angle θ of the E-beam relative to the sealed packages. The desired angle θ is one which has been previously determined to allow sterilization of the entire assembly 71 (combination of stent 10 and catheter 72) to a specified sterility assurance level while minimizing degradation to the stent.

Proper orientation of transport container 110 on sterilization platform 82, wherein angle φ corresponds to the desired angle θ of the E-beam, can be achieved by making rear face 104 of transport container 110 parallel to arrow 84, which represents the direction of relative movement between sterilization platform 82 and radiation source 86. It is to be understood that, with transport container 110 oriented as described above, the stent-catheter assemblies contained within the transport container 110 are oriented in the same way as described in connection with FIGS. 5 and 6 and, therefore, can be sterilized with the same radiation dosages, number of passes across radiation source 86, and other process variables used for FIGS. 5 and 6 in order to achieve the same results.

In a presently preferred embodiment, sterilization is completed with a single pass across radiation source 86. In other embodiments, sterilization is completed by performing two passes in order to increase uniformity of radiation exposure, wherein each pass is performed with a different face of package 70 facing toward radiation source 86. In other embodiments, sterilization is completed with up to four passes, wherein each pass is performed at a relatively lower radiation level in order to minimize the build up of heat generated by the radiation with a period of cooling between passes.

In other embodiments, transport container 110 can be added to the methods and apparatuses described in U.S. patent application Ser. No. 11/809,511 in order to achieve similar results but with improved reliability.

To help ensure proper orientation of transport container 110 on sterilization platform 82, transport container 110 can include visual indicia 130 on its exterior. Examples of visual indicia 130 include without limitation an adhesive label or printed arrow. Visual indicia 130 can, for example, provide an indication of which face of transport container 110 must face upward when placed on sterilization platform 82. In addition, sterilization platform 82 can include visual and/or physical indicia 132. Examples of visual and physical indicia 132 include without limitation an adhesive label, printed line, raised fence, or protruding bump which is used by personnel at the sterilization facility to place transport container 110 on the sterilization platform 82 so as to be at the proper orientation and distance relative to radiation source 86.

After sterilization, transport container 110 can be shipped from the sterilization facility to its point of origin, such as the facility which manufactures stents. Thereafter, packages 70 are removed from transport container 110 and prepared for storage or for delivery to a consumer, such as a hospital. Transport container 110 and dummy loads 108 are reusable. Dummy loads 108 are set aside and can be used again to sterilize additional packages 70 at a later time. The transport container 110 is also set aside and can be used again to sterilize additional packages at a later time.

Though the above embodiments are described in connection with stents, the above described methods and apparatuses can be applied generally to other types of implantable medical devices which may require tight control of radiation exposure. Examples of implantable medical devices include, but are not limited to, self-expandable stents, balloon-expandable stents, stent-grafts, grafts (e.g., aortic grafts), artificial heart valves, cerebrospinal fluid shunts, pacemaker electrodes, and endocardial leads. The underlying structure or substrate of the device can be of virtually any design.

Though the above embodiments are described in connection with E-beam radiation, it will be appreciated that the methods and apparatuses described above can be used for other types of radiation. Examples of other types of radiation include without limitation gamma radiation, ion beam, and x-ray. In other embodiments, radiation source 86 emits gamma radiation, ion beam, or x-ray.

In some embodiments, no dummy loads 108 are placed at the ends of stack 94.

EXAMPLE

At a stent manufacturing facility, a stack of packages containing polymer stent-catheter assemblies are arranged with a tilt angle φ of about 45 degrees within a transport box. Each package is oriented within the stack such that the polymer stent is close to the opening of the transport box (i.e., close to the front of the stack when eventually oriented on a sterilization platform, similar to the stent orientation within package 70b in FIG. 6). Each package has an average density of about 0.1 g/cm$^3$. A dummy load is placed at each of the stack of packages. Each dummy load is a block of polyethylene foam having a density of 96 kg/m$^3$ and is oriented with a tilt angle φ of about 45 degrees within the transport box. After all packages and dummy loads are placed in the transport box, the lid of the transport box is sealed shut and the transport box is transported to a sterilization facility. At the sterilization facility, the transport box is cooled so that its contents reach minus 15 degrees C. Next, the lid of the transport box is opened and the transport box is placed on the sterilization platform so that the opening faces the sterilization source. The transport box is oriented to achieve an angle θ of about 45 degrees relative to the radiation source. The radiation source is set to provide a radiation dose from about 20 kGy to about 31 kGy in order to achieve a sterility assurance level of 10$^{-6}$ with a single pass of the transport box across the radiation source. After radiation exposure is completed, the lid of the transport box is sealed shut and the transport box is transported back to the stent manufacturing facility where the sterilized packages are removed from the transport box.

While several particular forms of the invention have been illustrated and described, it will also be apparent that various modifications can be made without departing from the scope of the invention. It is also contemplated that various combinations or subcombinations of the specific features and aspects of the disclosed embodiments can be combined with or substituted for one another in order to form varying modes of the invention. Accordingly, it is not intended that the invention be limited, except as by the appended claims.

The invention claimed is:

1. A method of sterilizing medical devices, the method comprising:
    placing packages into a transport box, each package containing at least one medical device, the packages partially shielding each other, each package having a corner portion with two exposed corner surfaces that are not shielded by an adjacent package and are out of contact with the transport box, the transport box having an interior space occupied by the packages, the interior space sized to keep the packages from shifting in position within the transport box when the transport box is in a closed state; followed by
    sending the transport box, with the packages therein, to a sterilization facility,
    wherein the transport box has a pivoting lid that is movable to a closed position in which the transport box is in the closed state and movable to an open position in which the transport box is in an open state.

2. The method of claim 1, wherein each package, when in the transport box, has a contact surface that touches and is shielded by an adjacent package, and wherein the contact surface and the exposed corner surfaces of each package are the same for an adjacent package.

3. The method of claim 1, wherein e packages form a stack in the transport box, and the method further comprises placing a dummy load in the transport box at each end of the stack.

4. The method of claim 3, wherein each package, when in the transport box, has contact surfaces that touch and are shielded by an adjacent package and/or dummy load, and wherein the contact surfaces and the exposed corner surfaces of each package are the same for all the packages.

5. The method of claim 1, further comprising:
    placing the transport box, with the packages therein, on a sterilization platform housed in the sterilization facility; and
    causing the sterilization platform and a radiation source to move relative to each other so that the transport box, with the packages therein, passes across the radiation source and is exposed to radiation.

6. The method of claim 5, wherein the placing of the transport box on the sterilization platform includes placing the transport box such that a primary side of each package is at an oblique angle θ to a central axis of radiation from the radiation source.

7. The method of claim 5, wherein the placing of the packages in the transport box includes orienting each package such that a primary side of each package is at an oblique angle φ to an interior face of the transport box.

8. The method of claim 7, wherein the placing of the transport box on the sterilization platform includes placing the transport box such that the primary side of each package is at an oblique angle θ to a central axis of radiation from the radiation source, the oblique angle θ being the same or about the same as the oblique angle φ.

9. The method of claim 5, wherein the causing of the sterilization platform and the radiation source to move relative to each other includes irradiating all of the packages in the transport box, and the method further comprises:
    after the irradiating, removing the packages from the transport box;
    placing additional packages into the transport box, each additional package containing at least one medical device, the additional packages partially shielding each other, each additional package having a corner portion with two exposed corner surfaces that are not shielded by an adjacent one of the additional packages and are out of contact with the transport box, the interior space of the transport box sized to keep the additional packages from shifting in position relative to each other within the transport box when the transport box is in the closed state; followed by
    placing the transport box, with the additional packages therein, on the sterilization platform; and
    causing the sterilization platform and the radiation source to move relative to each other so that the transport box, with the additional packages therein, passes across the radiation source and is exposed to radiation.

10. The method of claim 5, wherein the transport box is in the open state while simultaneously on the sterilization platform and being exposed to radiation.

11. The method of claim 5, wherein, when the transport box passes across the radiation source, the transport box is in the open state and does not shield packages from radiation emitted directly from the radiation source.

12. The method of claim 1, wherein the transport box has a rear face located opposite the pivoting lid, a first edge of each packages rests on the rear face when the packages are placed in the transport box, an interior width of the transport box is the same as a dimension of each package along the first edge, a second edge of each package is disposed adjacent to the lid when the lid is in the closed position.

13. The method of claim 12, wherein the second edge of each package contacts the lid when the lid is in the closed position.

14. A method of sterilizing medical devices, the method comprising:
    stacking packages side-by-side in a transport box such that a first side of each package includes a contact surface portion, in contact with an adjacent package or a dummy load, and an exposed surface portion, not in contact with the adjacent package or the dummy load, the transport box having an interior space occupied by the packages, the interior space sized to keep the packages from shifting in position within the transport box when the transport box is in a closed state,
    wherein the transport box has a pivoting lid that is movable to a closed position in which the transport box is in the closed state and movable to an open position in which the transport box is in an open state.

15. The method of claim 14, wherein the packages form a stack within the transport box, and the method further comprises placing a dummy load at an end of the stack.

16. The method of claim 14, wherein after the stacking the method further comprises:
    placing the transport box, with the packages carried therein, adjacent a radiation source;
    moving the packages, while carried in the transport box, relative to the radiation source in order to expose the packages to radiation; and
    opening the transport box to the open state, wherein the transport box passes across the radiation source while in the open state.

17. The method of claim 16, wherein the transport box does not shield the packages from radiation emitted directly from the radiation source.

18. The method of claim 14, further comprising:
after the stacking of the packages side-by-side in the transport box, sending the transport box, while in the closed state, to a sterilization facility which houses a sterilization platform.

19. The method of claim 14, wherein the stacking of the packages is performed such that the first side is at an oblique angle $\phi$ to an interior face of the transport box.

20. The method of claim 14, wherein the stacking of the packages is performed such that a second side of each package, located opposite the first side, includes a contact surface portion, in contact with an adjacent package or the dummy load, and an exposed surface portion, not in contact with the adjacent package or the dummy load.

21. The method of claim 14, further comprising:
after the packages have been sterilized in the transport box, removing the packages from the transport box; and
stacking additional packages side-by-side in the transport box such that a first side of each additional package includes a contact surface portion, in contact with an adjacent one of the additional packages or the dummy load, and an exposed surface portion, not in contact with the adjacent one of the additional package or the dummy load, the interior space of the transport box sized to keep the additional packages from shifting in position within the transport box when the transport box is in the closed state.

22. The method of claim 21, further comprising:
after the packages have been sterilized in the transport box, removing the dummy load from the transport box; and
wherein the additional packages forms a stack within the transport box, and the method further comprises placing the dummy load at an end of the stack.

23. The method of claim 14, wherein the transport box has a rear face located opposite the pivoting lid, a first edge of each package rests on the rear face when the packages are stacked in the transport box an interior width of the transport box is the same as a dimension of each package along the first edge, a second edge of each package is disposed adjacent to the lid when the lid is in the closed position.

24. The method of claim 23, wherein the second edge of each package contacts the lid when the lid is in the closed position.

* * * * *